US 7,723,689 B2

(12) United States Patent
Vija

(10) Patent No.: US 7,723,689 B2
(45) Date of Patent: May 25, 2010

(54) OPEN LIMITED ORBITING TOMOGRAPHIC IMAGING SYSTEM

(75) Inventor: A Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 614 days.

(21) Appl. No.: 11/524,796

(22) Filed: Sep. 21, 2006

(65) Prior Publication Data

US 2008/0073540 A1    Mar. 27, 2008

(51) Int. Cl.
*G01T 1/166* (2006.01)
(52) U.S. Cl. .................................. 250/363.05
(58) Field of Classification Search ............. 250/363.05
See application file for complete search history.

(56) References Cited

U.S. PATENT DOCUMENTS

| | | | |
|---|---|---|---|
| 4,613,122 A | 9/1986 | Manabe | |
| 4,645,933 A | 2/1987 | Gambini et al. | |
| 4,652,758 A | 3/1987 | Barfod | |
| 4,652,759 A | 3/1987 | Platz | |
| 5,519,222 A * | 5/1996 | Besett ................... | 250/363.04 |
| 5,757,006 A | 5/1998 | DeVito et al. | |
| 5,923,038 A * | 7/1999 | DiFilippo et al. ...... | 250/363.04 |
| 6,150,662 A * | 11/2000 | Hug et al. .............. | 250/363.05 |
| 6,184,530 B1 | 2/2001 | Hines et al. | |
| 6,211,523 B1 * | 4/2001 | Gagnon .................. | 250/363.04 |
| 6,242,743 B1 | 6/2001 | DeVito et al. | |
| 6,774,371 B2 * | 8/2004 | Garrard et al. ......... | 250/363.08 |
| 6,927,395 B2 * | 8/2005 | Koops et al. ........... | 250/363.08 |
| 7,242,002 B2 * | 7/2007 | Blevis et al. ........... | 250/363.05 |
| 2003/0230724 A1 * | 12/2003 | Koops et al. ........... | 250/363.08 |
| 2004/0262525 A1 * | 12/2004 | Yunker et al. .......... | 250/363.08 |
| 2006/0180766 A1 * | 8/2006 | Difilippo ............... | 250/363.09 |
| 2008/0073539 A1 | 3/2008 | Vija | |

OTHER PUBLICATIONS

"Principles of instrumentation in SPECT", J Nucl Med Technol 13 (1985).
Computed Tomography in Nuclear Medicine by John Keyes, (chapter in) Computer Methods, C. V. Mosley, St. Louis, 1977, pp. 130-138.
"Single Photon Emission Computed Tomography," by Bernard Oppenheim and Robert Appledown, (chapter in) Effective Use of Computers in Nuclear Medicine, Michael Gelfand and Stephen Thomas, McGraw-Hill Book Co., New York 1988, pp. 31-74.
Orlov, S. S., Theory of three dimensional reconstruction ii: the recovery of operator, Soviet Phys. Crystallogr, 20:429-433 (1976).
Natterer, F. and Wubbeling, F., Mathematical Methods in Image Reconstruction. SIAM, Philadelphia, Pa. (2001).

* cited by examiner

*Primary Examiner*—David P Porta
*Assistant Examiner*—Marcus H Taningco
(74) *Attorney, Agent, or Firm*—Peter L. Kendall

(57) ABSTRACT

A radiographic three dimensional imaging apparatus capable of focusing on a center of rotation point, includes at least two gamma ray detectors, each having a radiation input face, with each detector positioned on a linear path, wherein each detector is movable along the detector's linear path, while simultaneously swiveling to maintain the detector's input face towards the rotation point. The apparatus allows for organ-targeted tomography as a virtual center of rotation can be placed arbitrarily with respect to a patient, constrained only by the physical limits of the detector motion.

26 Claims, 6 Drawing Sheets

OPEN LIMITED ORBITING TOMOGRAPHIC IMAGING SYSTEM

BACKGROUND OF THE INVENTION

1. Field of the Invention

The invention relates generally to imaging systems and more particularly to three dimensional imaging systems for use in nuclear medicine.

2. Description of Background Art

Multiple gamma ray cameras often are used in nuclear medicine to generate high quality three dimensional images for clinical studies such as brain studies, heart studies, total body, bone and other diagnostic studies, using SPECT (Single Photon Emission Computed Tomography), or PET (Positron Emission Tomography). One challenge in this field is to provide a three dimensional imaging apparatus for multiple cameras and/or camera movements to allow for high patient throughput for both economic and therapeutic reasons. Diagnosis cost is reduced if more patients can be tested per unit time. For very ill patients or patients in intensive care the time for image acquisition should be minimized in the interests of patient health and comfort.

Accordingly, a variety of gantries, gamma detector types and detector orbital movements have been exploited. Modern gamma ray cameras utilize detectors, such as Anger cameras, that have a wide field of view to allow imaging the full width of the body of a patient at each angular view or stop without requiring rectilinear scanning. These detectors generally use thick lead collimators to acquire projection data. The collimators often are positioned close to the patient to generate high resolution images. The image data acquired by the detectors are processed by a computer to reconstruct a tomographic image. Techniques for processing image data are well-known and described, for example, in "Principles of Instrumentation in SPECT" by Robert Eisner, Journal of Nuclear Medicine, Vol. 13, #1, Mar. 1985, pp. 23-31; Computed Tomography in Nuclear Medicine" by John Keyes, (chapter in) Computer Methods, C. V. Mosley, St. Louis, 1977, pp. 130-138; and "Single Photon Emission Computed Tomography," by Bernard Oppenheim and Robert Appledown, (chapter in) Effective Use of Computers in Nuclear Medicine, Michael Gelfand and Stephen Thomas, McGraw-Hill Book Co., New York 1988, pp. 31-74.

To facilitate faster detection time, dual-head systems with detectors oriented at a fixed angle of 180°, and triple-head systems, with three detectors oriented at fixed angles of 120° have been used, particularly for SPECT gamma ray imaging. Further, detectors on a gantry may rotate about the patient, thereby defining a lateral axis as the mechanical axis of rotation aligned with a computer matrix for reconstructing the SPECT images.

Acquisition of data for a total body scan typically involves movement of detector(s) along the patient's body and dual head or triple head systems allow shortened time via simultaneous data capture. However, high quality images require angular sampling of data over typically at least 180 degrees around the focal point of an imaging apparatus. Thus, a high-quality SPECT for brain, bone, or liver studies for example, generally requires a view taken along a complete 360 degree circle (360° scan) around the body of the patient. Typically, about 64 to 128 angular views or stops are required to acquire the image data, using a single detector. For cardiac SPECT imaging, typically at least 32 stops over a 180 degree arc about the patient's body (180° scan) may be required.

Generally, rotating gantries are used that move detector(s) within an orbit, allowing multiple positions for the same detector(s). See, for example, U.S. Pat. Nos. 6,242,743; 5,757,006, and see U.S. Pat. Nos. 4,652,759; 4,652,758; 4,645,933, 6,184,530 and 4,613,122, the contents of which are incorporated by reference in their entireties. Unfortunately, large rotating gantries in particular, such as that described in U.S. Pat. No. 6,184,530, generally require heavy drive gear rings and other parts and tend towards large gantries, which makes the overall apparatus quite large and less open to the patient.

SUMMARY OF THE INVENTION

An object of embodiments of the invention is to provide a SPECT system that can be used with a relatively simple and inexpensive adjustable gantry. To this end, two or more detector cameras are movable within the gantry with respect to the imaging axis, and thus the amount of gantry motion required to accommodate small patients and to cover a radius around a rotation point is reduced.

Embodiments thus provide an apparatus that images body structure(s) using a gantry of more limited movement. In an embodiment, a gantry with limited movement (e.g. less than 180 degrees) moves one or more tracked detector imagers partly around a center of rotation point. The detector imagers separately move within a plane and/or within a line, while swiveling to face the rotation point. In another embodiment, the gantry does not rotate the detector within a plane at all, but detector imagers ("detectors") on the gantry separately move within a plane and/or along separate line(s). Such arrangement of movements allows detector positioning at substantially (i.e. within plus or minus 10%) 180 degrees or substantially 360 degrees around a patient, while minimizing or even eliminating gantry movement.

An embodiment provides a radiographic three dimensional imaging apparatus capable of focusing on a center of rotation point, comprising at least two gamma ray detectors, each having a radiation input face, with each detector positioned on a linear path, wherein each detector is movable along the detector's linear path, while simultaneously swiveling to maintain the detector's input face towards the rotation point. Another embodiment provides a radiographic three dimensional imaging apparatus capable of focusing on a center of rotation point, comprising: at least two gamma ray detectors, each having a radiation input face, with each detector positioned and movable within a plane, while simultaneously swiveling to maintain the detector's input face towards the rotation point. Yet another embodiment provides a radiographic three dimensional imaging apparatus capable of focusing on a center of rotation point, comprising at least two gamma ray detectors, each having a radiation input face with an adjustable collimator, with each detector positioned on a linear path, wherein each detector is movable along the detector's linear path, while simultaneously swiveling to maintain the detector's input face towards the rotation point. Yet another embodiment provides an apparatus as described above, with a collimator of adjustable resolution.

Yet another embodiment provides an improvement to a single photon emission computed tomography apparatus, the improvement comprising adding one or more gamma ray detectors to a gantry of the apparatus, the added detectors simultaneously able to swivel and move along linear paths tangent to the gantry rotation point. Yet another embodiment provides a single photon emission computed tomography apparatus with limited gantry motion, comprising a gantry for positioning gamma ray detectors around a center of rotation point, the gantry having rotation movement limited to less than 90 degrees, wherein the gantry contains at least two gamma ray detectors, wherein the at least two gamma ray detectors are movable within a plane while simultaneously swiveling to maintain the detectors' input faces towards the rotation point. Other embodiments will be appreciated by a reading of the specification.

DETAILED DESCRIPTION OF THE PREFERRED EMBODIMENTS

Figure 1A:
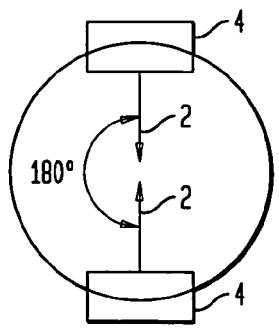
FIGS. 1A-1F shows prior art with opposite and radially spaced, gantry mounted detectors.
Figure 1B:
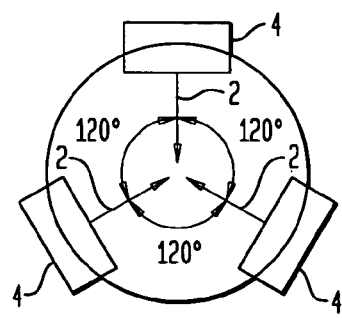
Figure 1C:
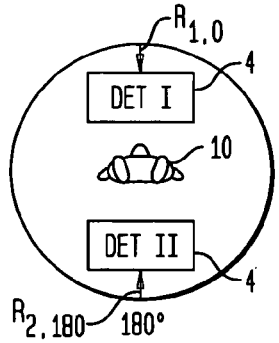
Figure 1D:
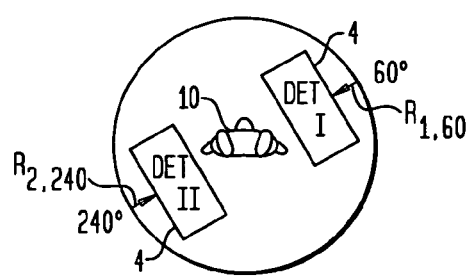
Figure 1E:
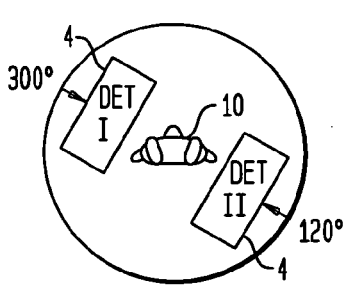
Figure 1F:
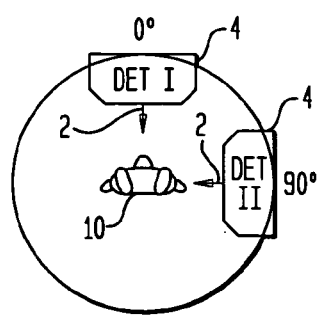
Figure 2:
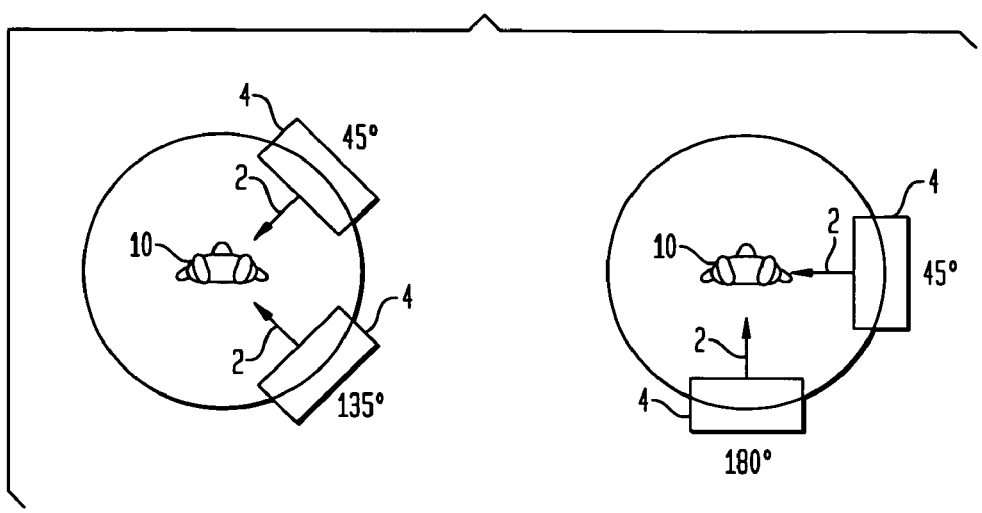
FIG. 2 shows prior art with gantry mounted detectors that operate simultaneously.
Figure 3:
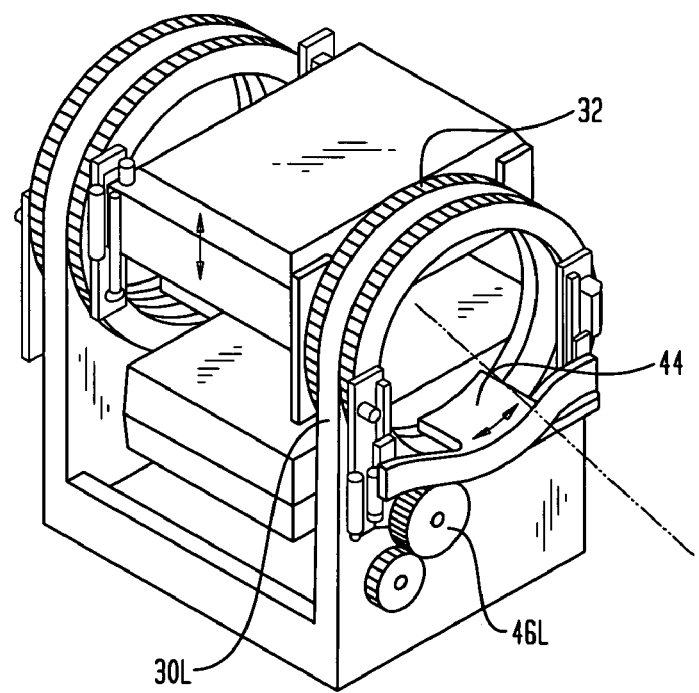
FIG. 3 shows an apparatus with a gantry and large gears for movement.

Prior art systems for single photon emission computed tomography generally are limited to multiple fixed position gamma detectors, or detectors mounted within a gantry that rotates through a plane and around a center of rotation point. The latter technique is exemplified in U.S. Pat. No. 6,184,530, which shows prior art configurations of 180° and 120° oriented detectors (see FIGS. 1A-1E) and presents an alternative wherein gamma detectors with fixed position with respect to each other are located 90 degrees apart and rotated together, for decreased analysis time (see FIG. 2). Rotation of the entire gantry with two or more detectors in fixed position with respect to each other particularly places constraints on apparatus design. A gantry for such typical prior art system generally is large and covered, as exemplified by the prior art apparatus depicted in FIG. 3.

Linear Motion Plus Swivel Systems

Figure 4A:
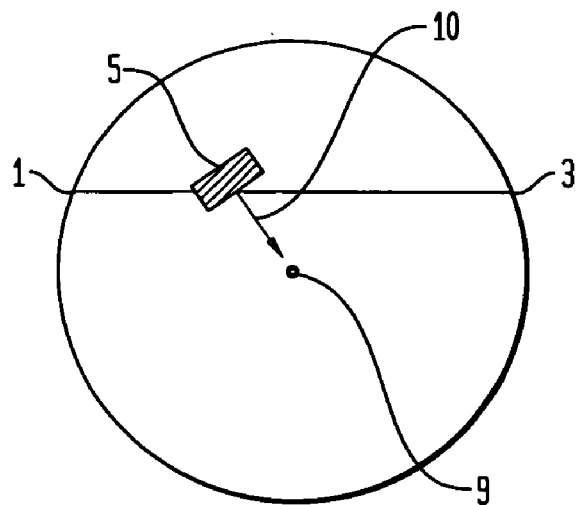
FIG. 4A and FIG. 4B show representative placement of movable detectors according to an embodiment of the invention.

In contrast to the fixed or rotated detectors, embodiments of the invention taught herein alleviate disadvantages of the rotating gantry systems by a combination of 1) moving gamma detectors within the gantry (such as on linear tracks), while 2) swiveling, or tilting the detectors individually, to maintain imaging focus on the rotation point. FIG. 4a shows how a circular orbiting detector path from position 1 to 3 is replaced by a linear path where detector 5 swivels to maintain its face pointing toward a center of rotation 9 for the desired arc. FIG. 4a assumes a parallel hole collimator geometry. Thus the center of rotation 9 is defined by the intersection of ray 10 perpendicular to the face of detector 5.

Figure 4B:
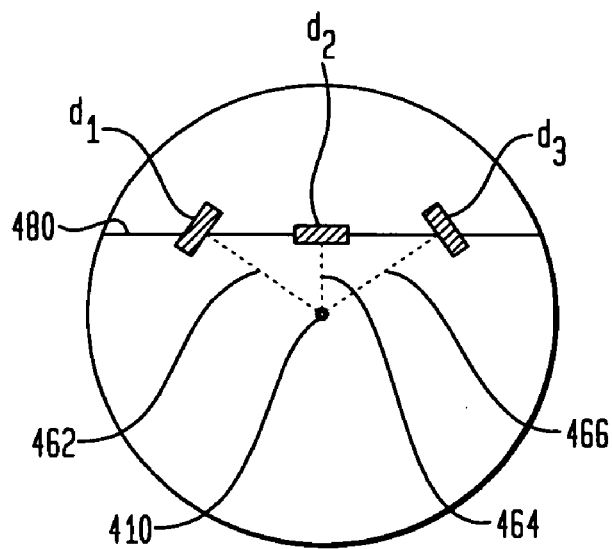

Desirably, two or more detectors or, "imagers" as they commonly are called in SPECT field, have limited size for such movement and swiveling, and ideally are spaced at least one detector diameter apart, as shown in FIG. 4b. Center of rotation point 410 shown in FIG. 4b is the focus point for detectors d1, d2 and d3, which have smaller dimensions than the inter-detector spacings shown in this figure. The position of each detector and the orthogonal lines 462, 464 and 466 to point 410 are affected by the longitudinal spacings of the detectors along line 480, which are adjustable according to embodiments of the invention.

The detectors may swivel or tilt about their local axis lines 462, 464, 466 and thereby maintain their focus towards center point 410. In a desirable embodiment one or more additional criteria are considered and met such as summarized as Orlov conditions for proper imaging, such as the conditions described in Orlov, S. S., Theory of three dimensional reconstruction ii: the recovery of operator, *Soviet Phys. Crystallogr,* 20:429-433 (1976), and more recently in Natterer, F. and Wübbeling, F., *Mathematical Methods in Image Reconstruction.* SIAM, Philadelphia, Pa. (2001). Such criteria specifically are incorporated herein by reference in their entireties and are not separately listed here for space reasons.

Figure 5A:
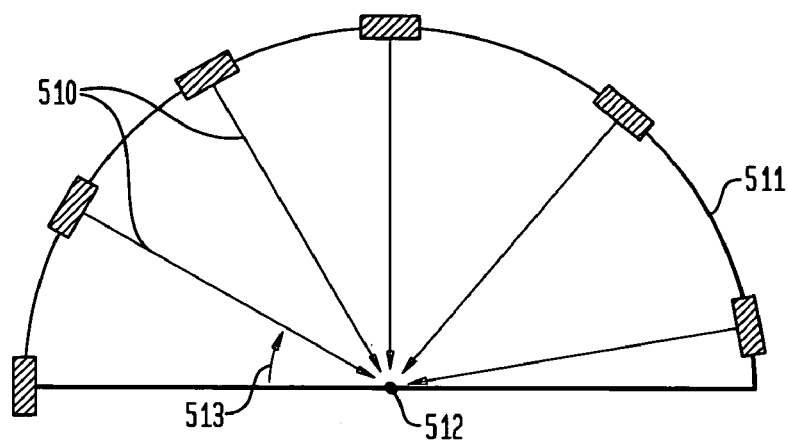
FIG. 5A and FIG. 5B show positions of detectors according to other embodiments of the invention.
Figure 5B:
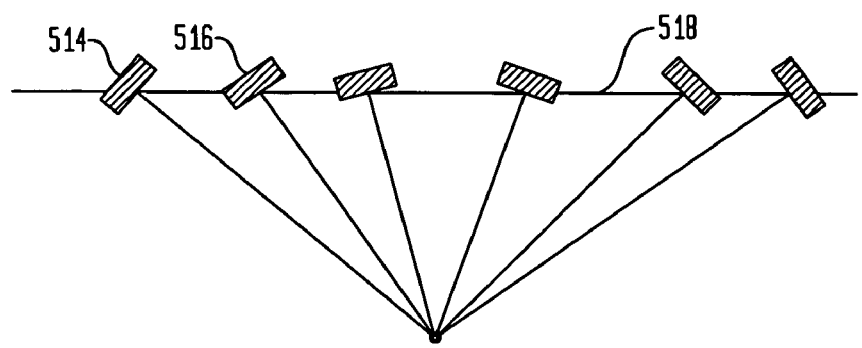

To obtain a desired resolution for resolving a structure of size D, for example, an angle 513 and spatial sampling distance δ distributed over an arc that fulfills Orlov's conditions as shown in FIG. 5a must be maintained. Arrows 510 in this figure represent view vectors between detectors (arranged on arc 511) and rotation point 512. The view vectors are separated by minimum angle 513 as shown in FIG. 5a. FIG. 5b shows how a detector face plane can be reoriented to maintain focus on the center rotation point. In an embodiment, detectors should be able to sample at least approximately (e.g. within 10% of) 180 degrees around the focus point. Preferably detectors should sample 360 degrees around the focus point. Preferably a minimum of two detectors 514 and 515 are maneuverable as shown on track 516 in FIG. 5b to cover (in combination) at least about 180 degrees and more preferably up to approximately 360 degrees. Other positions shown on track 516 represent representative placement of detectors 514 and 515. By mounting two or more detectors on one, two or more linear tracks such coverage around the center of rotation point can be obtained without rotating the gantry.

Figure 6A:
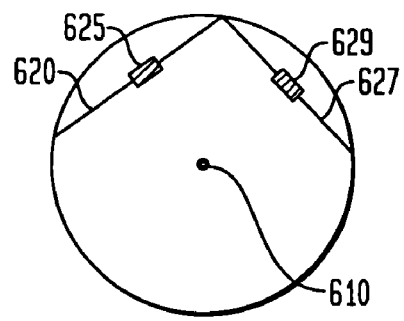
FIGS. 6A, 6B and 6c show detectors on tracks around a rotation point according to further embodiments of the invention.
Figure 6B:
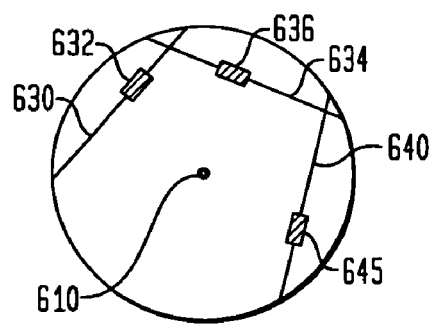
Figure 6C:
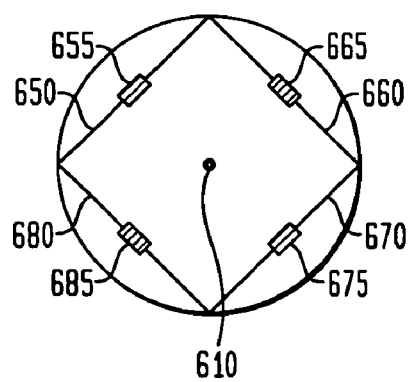

Further exemplary embodiments of multiple detectors that independently move along tracks are shown in FIG. 6A to 6D, which show a side view of the interior of a three dimensional imager along axis 610 of the rotation point. FIG. 6A shows track 620 with movable detector 625, and track 627 with movable detector 629 that swivel towards rotation point 610 while moving along these respective tracks. FIG. 6B shows track 630 with movable detector 632, track 634 with movable detector 636 and track 640 with movable detector 645. FIG. 6C shows track 650 with movable detector 655, track 660 with movable detector 665, track 670 with movable detector 675 and track 680 with movable detector 685. In an alternate embodiment one or more detectors move along a nonlinear track, such as an ellipsoid track, oval track, or round track.

Detectors and Their Collimators

A wide variety of detectors are available and may be used in accordance with the present invention. Generally, a detector will have a side that receives incident gamma radiation for interaction with a crystal or other scintillant material, followed by two dimensional position sensitive detectors, for determining the spatial positioning of the gamma ray in the detector head. Anger cameras and other detectors are used in conjunction with a collimator, to establish the direction of gamma rays to be detected. In an embodiment only the detector moves along a track in the gantry, and a collimator for the detector exists in elongated form along the track, or multiple collimators are positioned at separate stations along the track. Desirably, each collimator at each station is positioned or constructed to provide a different focus as needed to compensate for the distance of the detector from the imaged target.

In another embodiment, a detector and its collimator move together along the track and the collimator optionally remains in the same relative location to the detector as the detector swivels. In yet another embodiment, a gap between the collimator and the detector is set as needed to adjust focusing to compensate for distance away from the target.

The size of the detector measured as the available area s for imaging shall be optimized as to obtain an untruncated planar projection image of either a particular organ, e.g. heart (e.g. 400 cm$^2$) or the entire body (thus large area detectors). The present invention is best suited for small organs, such as heart, prostate etc.

Movement of detectors and their placement more than one diameter apart for focusing are facilitated by the small size of detectors that preferably are used. Currently preferred detectors are any current scintillation detector (e.g. NaI and PMT combination), or solid state detector, e.g., CZT, CdT, etc. with an acceptably small footprint. The image reconstruction algorithm now simply incorporates the particular motion, e.g. the normal vector of the detector face at each time with respect to some coordinate system. An alternative option would be the use of an adaptive collimator which would attempt to change the resolution as the detector moves linearly and swivels.

Figure 7A:
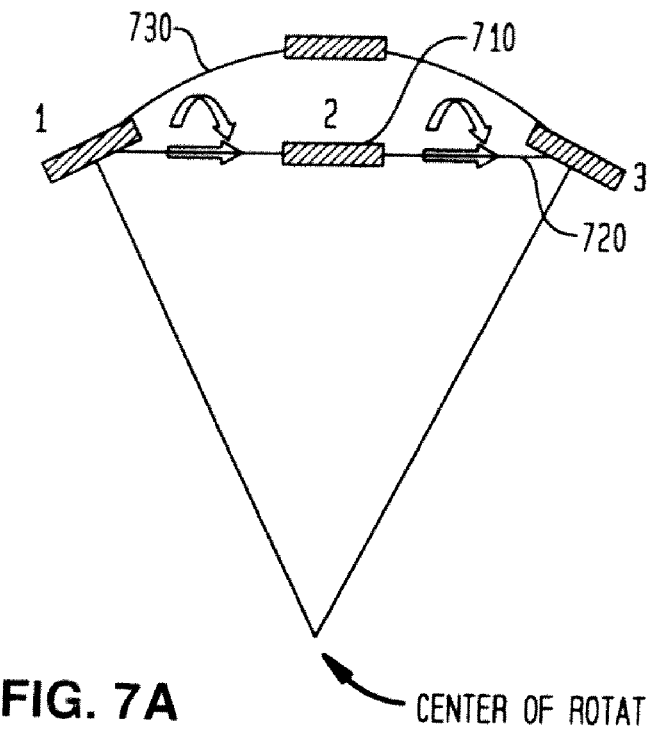
FIG. 7A and FIG. 7B show detail of detector movement and collimator design, respectively, according to still further embodiments of the invention.
Figure 7B:
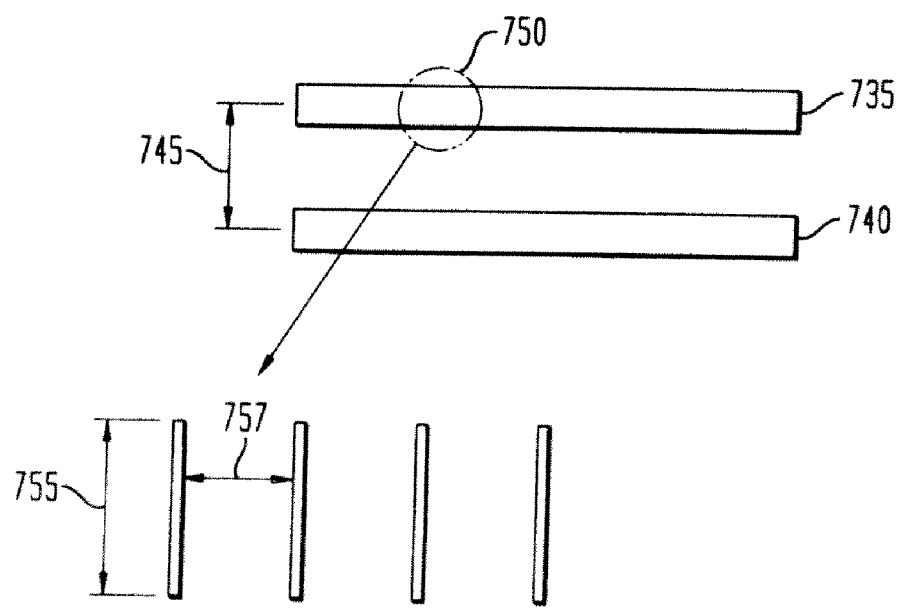

FIG. 7A depicts a detector 710 that moves while swiveling along track 720 to positions 1 and 3, which are located on arc 730. A particularly desirable embodiment utilizes collimators of variable resolution, to accommodate detectors with variable distances from a center rotation (focus) point. A desirable collimator design is shown in FIG. 7B. Septa 735 and 740 shown in this figure as spaced apart by distance 745 are positioned parallel to the face of a detector and between the detector and an imaged body. Septa 735 and 740 contain vertically spaced gamma blocking material such as lead sheets. Magnified portion 750 reveals a region 760 of plates having height 755 and interpolated spacings 757. Desirably, distance 745 is adjusted proportionately with distance of the detector from a rotation axis. Dimensions 745, 755 and 757 are variable and adjusted as further explained in U.S. application No. [2006P07898US], entitled * and filed on *, the entire contents of which specifically are incorporated herein by reference.

The combination of track movements with rotation minimizes gantry movement needed to cover the perimeter of a sample space, thus permitting the use of simpler and smaller gantry gears and part sizes while potentiating the use of more open equipment for placement of patients.

The methods and apparatus described above are exemplary only and do not limit the scope of the claims. Various modifications can be made by skilled artisans, which fall within the scope of the invention.

I claim:

1. A radiographic three dimensional imaging apparatus for focusing on a center of rotation point for use in emission tomography, comprising:
    at least two gamma ray detectors, each having a radiation input face, with each detector positioned on a linear path, wherein each detector moves during tomographic imaging along the detector's linear path, while simultaneously swiveling to maintain the detector's input face towards the rotation point.

2. The radiographic three dimensional imaging apparatus of claim 1, wherein the at least two gamma ray detectors independently move along a common linear path.

3. The radiographic three dimensional imaging apparatus of claim 1, wherein each linear path is a track and said track rotates around the center of rotation point.

4. The radiographic three dimensional imaging apparatus of claim 1, further comprising a movable gantry that contains a linear track for moving the at least two gamma ray detectors, and wherein the at least two gamma ray detectors move to positions at least 180 degrees around the center of rotation point.

5. The radiographic three dimensional imaging apparatus of claim 1, wherein each of the at least two gamma ray detectors comprises an adjustable collimator.

6. The radiographic three dimensional imaging apparatus of claim 5, wherein each collimator is adjustable in resolution.

7. The radiographic three dimensional imaging apparatus of claim 1, wherein each of the at least two gamma ray detectors is positioned on a common linear path.

8. The radiographic three dimensional imaging apparatus of claim 1, comprising a first set of at least two gamma ray detectors that move along a first linear path and a second set of at least two gamma ray detectors that are movable along a second linear path.

9. The radiographic three dimensional imaging apparatus of claim 8, wherein the first and second sets of gamma ray detectors are mounted on a common gantry.

10. The radiographic three dimensional imaging apparatus of claim 9, wherein the gantry comprises a first linear track for moving the first set of at least two gamma ray detectors, and a second linear track for moving the second set of at least two gamma ray detectors and wherein the tracks are rotated around the rotation point.

11. The radiographic three dimensional imaging apparatus of claim 1, wherein each linear path is tangent to the center of rotation point.

12. A radiographic three dimensional imaging apparatus for focusing on a center of rotation point, comprising:
    at least two gamma ray detectors, each having a radiation input face, with each detector positioned and moves during tomographic imaging within a plane, while simultaneously swiveling to maintain the detector's input face towards the rotation point.

13. The radiographic three dimensional imaging apparatus of claim 12, wherein at least two detectors move within the same plane.

14. The radiographic three dimensional imaging apparatus of claim 12, wherein each of the at least two gamma ray detectors comprises an adjustable collimator.

15. The radiographic three dimensional imaging apparatus of claim 12, wherein the at least two gamma ray detectors move to positions that encompass at least 180 degrees around the center of rotation point.

16. An improvement to a single photon emission computed tomography apparatus having at least one gamma ray detector, the improvement comprising adding one or more gamma ray detectors to a gantry of the apparatus, the added detectors being able to simultaneously swivel and move during tomographic imaging along linear paths tangent to the gantry rotation point.

17. The improvement of claim 16, wherein at least two gamma ray detectors are added and are movable to positions that encompass at least 180 degrees around the center of rotation point.

18. A single photon emission computed tomography apparatus with limited gantry motion, comprising:
    a gantry for positioning gamma ray detectors around a center of rotation point, the gantry having rotation movement limited to less than 90 degrees,
    wherein the gantry contains at least two gamma ray detectors, wherein the at least two gamma ray detectors move during tomographic imaging within a plane while simultaneously swiveling to maintain the detectors' input faces towards the rotation point.

19. The radiographic three dimensional imaging apparatus of claim 18, wherein the at least two gamma ray detectors independently move along linear paths.

20. The radiographic three dimensional imaging apparatus of claim 19, wherein the at least two gamma ray detectors independently move along a common linear path.

21. The radiographic three dimensional imaging apparatus of claim 18, wherein the at least two gamma ray detectors move to positions that encompass substantially at least 180 degrees around the center of rotation point.

22. The radiographic three dimensional imaging apparatus of claim 18, wherein each of the at least two gamma ray detectors comprises an adjustable collimator.

23. The radiographic three dimensional imaging apparatus of claim 22, wherein each collimator is adjustable in resolution.

24. The radiographic three dimensional imaging apparatus of claim 18, having an open gantry structure.

25. A method of radiographic three dimensional imaging of a patient, comprising:
 placing the patient within an open gantry apparatus having a gantry that moves along the body axis of the patient, the gantry comprising at least two gamma ray detectors which move during tomographic imaging within respective tracks of the gantry, each detector radiation input face swivelable to maintain the radiation input face perpendicular to the patient, and
 activating the apparatus to move the detectors at least 180 degrees around the patient by translocation of the detectors within their tracks, while simultaneously swiveling the detectors to maintain their radiation input faces perpendicular to the patient.

26. The method of claim 25, further comprising the step of automatically adjusting collimator focus of collimators that are used to control radiation input to the detectors.

* * * * *